United States Patent
Bountra et al.

(10) Patent No.: US 6,548,507 B1
(45) Date of Patent: Apr. 15, 2003

(54) MEDICAL USE

(75) Inventors: Charanjit Bountra, Stevenage (GB); Malcolm Stuart Nobbs, Stevenage (GB)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/958,429

(22) PCT Filed: Apr. 7, 2000

(86) PCT No.: PCT/GB00/01320

§ 371 (c)(1),
(2), (4) Date: Oct. 9, 2001

(87) PCT Pub. No.: WO00/61231

PCT Pub. Date: Oct. 19, 2000

(30) Foreign Application Priority Data

Apr. 9, 1999 (GB) ............................................. 9907965

(51) Int. Cl.$^7$ .................. A61K 31/4965; A61K 31/505
(52) U.S. Cl. .................................. 514/255.06; 514/275
(58) Field of Search .............................. 514/55.06, 275

(56) References Cited

U.S. PATENT DOCUMENTS 6,071,970 A    6/2000   Meuller et al.

FOREIGN PATENT DOCUMENTS

| EP | 0 021 121 | | 1/1981 |
|---|---|---|---|
| WO | 94/18972 | | 9/1994 |
| WO | WO 97/09317 | * | 3/1997 |
| WO | WO 98/38174 | * | 9/1998 |
| WO | 99/41372 | | 8/1999 |
| WO | 02/11739 | | 2/2002 |

OTHER PUBLICATIONS

Casanovas, A. et al., "Prevention by lamotrigine, MK–801 and N.omega.–nitro–L–arginine methyl ester of motoneuron cell death after neonatal axotomy," Neuroscience, 71(2), 1996, pp. 313–325.

Meldrum, B. S. et al., "Sodium–channel blockade and glutamate release: The mechanism of cerebroprotection by lamotrigine, BW 1003C87 and BW 619C89," Pharmacol. Cereb. Ischemia, 5$^{th}$ (1994), 203–9.

McCleane, G., "Lamotrigine can reduce neurogenic pain associated with multiple sclerosis," Clinical Journal of Pain, 14 (3), Sep. 1998, pp. 269–270.

Hamill, O et al., "Pharmacology of Mechanogated Membrane Channels," Pharmacol. Reviews, 1996, 48(2), pp. 231–252.

Osborne, N et al., "Neuroprotection in Relation to Retinal Ischaemia and Relevance to Glaucoma," Survey of Opthalmology, 1999, 45(Suppl I), pp. S102–128.

Ritch, R., "Neuroprotection: is it applicable to glaucoma therapy?, " Current Opinion in Opthalmology, 2000, 11(2), pp. 78–84.

Gui–Rong, Li et al., "Modulation of cardiac NA$^+$current by gadolinium, a blocker of stretch–induced arrhythmias," American Physiological Soc.., 2001, vol. 280, pp. 272H–279H.

Hartwick, A., "Beyond Intraocular Pressure: Neuroprotective Strategies for Future Glaucoma Therapy," Opthalmology and Vision Science, Feb. 2001, 78(2), pp. 85–94.

Ettaiche, M. et al., "Riluzole Improves Functional Recovery after Ischemia in the Rat Retina," Investigative Opthalmology & Visual Science, 1999, 40(3), pp. 729–736.

Maingret, F. et al., TRAAK Is a Mammalian Neuronal Mechano–gated K$^+$ Channel, J. Biol. Chemistry, 1999, 274(3), pp. 1381–1387.

Agar, A. et al., "Pressure Related Apoptosis in Neuronal Cell Lines." J. Neuroscience Res., 2000, vol. 60, pp. 495–503.

Callaway, J. et al., "Incorporation of sodium channel blocking and free radical scavenging activities into a single drug, AM–36, results in profound inhibition of neuronal apoptosis," Brit. J. Phrmacol., Apr. 2001, vol. 132, pp. 1691–1698.

* cited by examiner

Primary Examiner—Raymond J. Henley, III
(74) Attorney, Agent, or Firm—Bonnie L. Doppenbrock

(57) ABSTRACT

The present invention relates to the use of sodium channel antagonists in the treatment of diseases mediated by, or exacerbated by, neuronal apoptosis, in particular sensory neuronal apoptosis.

15 Claims, 2 Drawing Sheets

MEDICAL USE

This application is filed pursuant to 35 U.S.C. §371 as a United States National Phase Application of International Application No. PCT/GB00/01320 filed Apr. 7, 2000, which claims priority from 9907965.9 filed Apr. 9, 1999.

The present invention relates to the use of sodium channel antagonists for the treatment of diseases mediated by, or exacerbated by, neuronal apoptosis, in particular sensory neuronal apoptosis.

BACKGROUND TO THE INVENTION

EP-0021121-A discloses a group of 3,5-diamino-6-(substituted phenyl)-1,2,4-triazines which are active in the treatment of central nervous system (CNS) disorders, for example in the treatment of epilepsy. One such triazine is 3,5-diamino-6-(2,3-dichlorophenyl)-1,2,4-triazine which is alternatively called lamotrigine.

EP-0372934-A discloses pyrimidine compounds useful in the treatment of CNS disorders. Example 14 of this application discloses 5-(2,3-dichlorophenyl)-6-trifluoromethyl-2,4-diaminopyrimidine, Example 18 of EP-0372934-A discloses 2,4-diamino-5-(2,3-dichlorophenyl)-6-fluoromethyl pyrimidine and Example 45 discloses 5-(2,6-dichlorophenyl)-6-methyl-2,4-diaminopyrimidine.

WO 97/09317 discloses the R(−) enantiomer of Example 18 of EP0372934-A, R(−)-2,4-diamino-5-(2,3-dichlorophenyl)-6-fluoromethyl pyrimidine, substantially free of the corresponding S(+)enantiomer, ie the compound of formula (I):

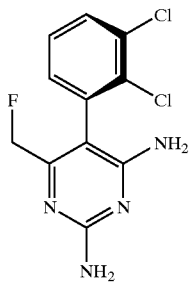

(I)

and acid addition salts thereof. This compound is also known as 4030W92.

WO98/38174 discloses pyrazine derivatives useful in the treatment of CNS disorders such as epilepsy, ie the compounds of formula (II):

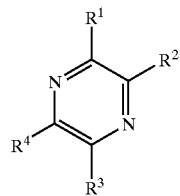

(II)

wherein
R$^1$ is selected from the group consisting of phenyl substituted by one or more halogen atoms, naphthyl and naphthyl substituted by one or more halogen atoms;
R$^2$ is selected from the group consisting of —NH$_2$ and —NHC(=O)R$^a$;
R$^3$ is selected from the group consisting of —NR$^b$R$^c$, —NHC(=O) R$^a$ and hydrogen;

R$^4$ is selected from the group consisting of hydrogen, —C$_{1-4}$ alkyl (preferably methyl), —C$_{1-4}$ alkyl (preferably methyl) substituted by one or more halogen atoms, —CN, —CH$_2$OH, —CH$_2$OR$^d$ and —CH$_2$S(O)$_x$R$^d$;
wherein
R$^a$ represents C$_{1-4}$ alkyl or C$_{3-7}$cycloalkyl, and
R$^b$ and R$^c$, which may be the same or different, are selected from hydrogen and C$_{1-4}$ alkyl, or together with the nitrogen atom to which they are attached, form a 6-membered nitrogen containing heterocycle, which heterocycle can be further substituted with one or more C$_{1-4}$ alkyl;
R$^d$ is selected from C$_{1-4}$ alkyl or C$_{1-4}$ alkyl substituted by one or more halogen atoms;
x is an integer zero, one or two;
and pharmaceutically acceptable derivatives thereof;
with the proviso that R$^1$ does not represent;

when R$^2$ is —NH$_2$, and both R$^3$ and R$^4$ are hydrogen. Particularly preferred is 2,6-diamino-3-(2,3,5-trichlorophenyl)pyrazine and pharmaceutically acceptable derivatives thereof.

WO99/32462 (PCT/EP98/08273) relates to a triazine compound which is useful in the treatment of central nervous system (CNS) diseases and disorders, ie the compound 5-amino-6-[2,3,5-trichlorophenyl]-1,2,4-triazine and pharmaceutically acceptable derivatives thereof.

WO00/12488 relates to carboxamide derivatives of pyrazine compounds such as those disclosed in WO98/38174 above, in particular 5-carboxamido-2,6-diamino-3-(2,3,5-trichlorophenyl)pyrazine.

The compounds of EP-0021121-A, EP-0372934-A, WO 97/09317, WO98/38174 WO99/32462 and WO00/12488 are sodium channel antagonists and therefore inhibit glutamate release.

Other sodium ion channel blockers include local anaesthetics/anti-dysrhythmics such as: lidocaine, mexilitine, ropivacaine, levobupivacaine; anti-convulsants such as: oxcarbazepine, topiramate, rufinamide, Co-102862, NW-1015; anti-ischaemics such as: sipatrigine, BIIR-561, BIII-890 and RS100642 and the analgesics such as: RS132943, details for which are all available from public databases such as Pharmaprojects.

It has been shown that the sodium channel antagonist, lamotrigine can prevent motorneuronal apoptotic cell death after neonatal axotomy: Casanovas A. et al Neuroscience Vol.71 No2 pp313–325 1996.

SUMMARY OF THE INVENTION

This invention relates to a parallel finding of much greater medical significance, that as a result of their ability to prevent neuronal apoptosis, sodium channel antagonists have a disease modifying effect and serve to halt or delay (slow down) the progression of disease as opposed to merely treating the symptoms of disease. For example, in the case of chronic pain, the sodium channel antagonists are able to halt or delay the underlying process which is causing the pain as well as ease the pain as demonstrated by behavioural testing. Thereby sodium channel antagonists can alter disease states in particular pain states mediated by sensory neuronal apoptosis. The ability to halt or delay the progression of disease states such as certain pain states, neurodegenerative diseases and inflammation, provides a significant breakthrough in the management of these otherwise poorly treated conditions.

Diseases mediated by, or exacerbated by neuronal apoptosis in particular sensory neuronal apoptosis, include: pain states, such as chronic pain states, following nerve insult due to, for example, injury or infection ie pain states associated with tissue damage; neurodegenerative diseases such as multiple sclerosis and Parkinson's disease; and inflammation. Sodium channel antagonists are of use in the treatment of these diseases and are also of use in delaying or halting the progression of these diseases.

It has previously been reported (see for example WO98/38186) that a deficiency of oxygen, for example in the region of a cerebral infarct, causes abnormally high concentrations of glutamic acid to be released. This leads to an overstimulation of excitatory amino acid receptors, eg NMDA receptors, resulting in the degeneration and death of neurones by way of a mechanism known as excitotoxicity. This process has been implicated in the pathophysiology of various neurodegenerative conditions. Sodium channel antagonists are known to inhibit glutamate release and therefore prevent the degeneration and death of neurones due to excitotoxicity.

However, neuronal apoptosis which occurs as a result of nerve damage is unrelated to nerve death due to excitotoxicity and it is not dependent on glutamic acid concentration. "Apoptosis" is a form of programmed cell death. A report from the Cell Death Nomenclature Committee (Apoptosis, Necrosis or Oncosis, Levin S. Toxicological Sciences 41 155–156 1998) defines the prelethal steps that follow cellular injury as apoptosis or oncosis (but not necrosis). Apoptosis is characterised by cytoplasmic shrinkage and karyorrhexis (The Pathways of Cell Death: Oncosis, Apoptosis and Necrosis Trump B. F. et al Toxicological Pathology 25 (1) 82–88 (1997)—chromatin is fragmented and packaged in bits of cell membrane. This shows up as densely coloured apoptotic bodies when visualised using a nuclear stain under the light microscope. Using electron microscopy the cytosol appears dense, endoplasmic reticulum may be dilated and mitochondria are condensed. Blebs in the cytoplasm will typically contain organelles. Breaks in the DNA that lead to karyorrhexis can be identified using gel electrophoresis or TUNEL staining but this alone is no longer considered adequate as cells stained positive using TUNEL, do not necessarily have the characteristics of apoptosis when studied at the electron microscopy level. The fluorescent nuclear stain Hoechst 33342 and light microscopic analysis is now considered the best technique. The most striking gross morphological characteristic is cell shrinkage.

As mentioned above, agents which prevent neuronal apoptosis have a disease modifying effect and serve to halt or delay the progression of disease.

The invention accordingly provides, in a first aspect the use of sodium channel antagonists in the treatment of diseases mediated by, or exacerbated by, neuronal apoptosis.

In a further aspect, the invention provides the use of sodium channel antagonists as disease modifying agents in diseases mediated by, or exacerbated by, neuronal apoptosis.

There is also provided as a further aspect of the invention the use of sodium channel antagonists in the preparation of a medicament for the treatment of diseases mediated by, or exacerbated by, neuronal apoptosis.

The invention has particular relevance in the case of sensory neuronal apoptosis and disease mediated or exacerbated by sensory neuronal apoptosis.

In an alternative or further aspect there is provided a method for the treatment of a mammal, including man, suffering from or susceptible to neuronal apoptosis, comprising administration of an effective amount of a sodium channel antagonist.

In an alternative or further aspect there is provided a method for the treatment of a mammal, including man, suffering from or susceptible to diseases mediated by, or exacerbated by, neuronal apoptosis, comprising administration of an effective amount of a sodium channel antagonist.

In a further aspect the invention provides the use of sodium channel antagonists in delaying or halting the progression of diseases selected from pain states following nerve insult, neurodegenerative diseases such as multiple sclerosis and Parkinson's, and inflammation.

In a further aspect the invention provides the use of sodium channel antagonists in the treatment of multiple sclerosis and inflammation.

It will be appreciated that reference to treatment is intended to include prophylaxis as well as the alleviation of established symptoms.

Preferred sodium channel antagonists for use in the instant invention include those compounds included in EP-0021121-A, EP-0372934-A, WO 97/09317, WO98/38174, WO99/32462 and WO00/12488, especially:

i) 3,5-diamino-6-(2,3-dichlorophenyl)-1,2,4-triazine called lamotrigine;

ii) R(−) and S(+)-2,4-diamino-5-(2,3-dichlorophenyl)-6-fluoromethylpyrimidine, called 4030W92 and 4082W92 respectively;

iii) 2,6-diamino-3-(2,3,5-trichlorophenyl)pyrazine;

iv) 5-amino-6-[2,3,5-trichlorophenyl]-1,2,4-triazine and pharmaceutically acceptable derivatives thereof;

v) (+/−)5-(2,3-dichlorophenyl)-6-trifluoromethyl-2,4-diaminopyrimidine and vi) (+/−)5-(2,6-dichlorophenyl)-6-methyl-2,4-diaminopyrimidine and their enantiomeric forms;

vii) 5-carboxamido-2,6-diamino-3-(2,3,5-trichlorophenyl)pyrazine.

Particularly preferred is R(−)-2,4-diamino-5-(2,3-dichlorophenyl)-6-fluoromethyl pyrimidine, substantially free of the corresponding S(+)enantiomer.

Sodium channel antagonists may be prepared according to methods known in the art, for example according to the methods described in EP-0021121-A, EP-0372934-A, WO 97/09317, WO98/38174, WO99/32462 and WO00/12488.

5-Amino-6-[2,3,5-trichlorophenyl]-1,2,4-triazine may be prepared under suitable reaction conditions from a compound of formula (IIa)

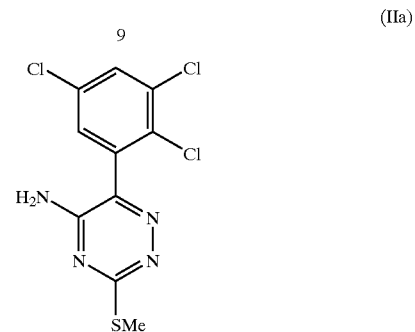

(IIa)

for example, by reduction, preferably using a reduction metal, such as Raney nickel, and a source of hydrogen, such as hydrazine monohydrate, in a suitable solvent, such as ethanol, preferably at elevated temperature, for example between 70–75° C.

The compound of formula (IIa) may suitably be prepared by reacting 2,3,5-trichlorobenzoyl cyanide with a S-methylthiosemicarbazide salt, preferably hydroiodide, in the presence of a dilute mineral acid, preferably dilute sulphuric acid.

Other sodium ion channel blockers for use in the invention include compounds such as: lidocaine, mexilitine, ropivacaine, levobupivacaine; compounds such as: oxcarbazepine, topiramate, rufinamide, Co-102862, NW-1015; compounds such as: sipatrigine and BIIR-561, BIII-890 and RS100642; and compounds such as RS132943, details for which are all available from public databases such as Pharmaprojects.

Suitable dose ranges are as described in the art, eg as in EP-0021121-A, EP-0372934-A, WO 97/09317, WO98/38174, WO99/32462 and WO00/12488. That is to say that for use according to the present invention the sodium channel antagonists may be used at doses appropriate for other conditions for which they are known to be useful. It will be appreciated that it may be necessary to make routine variations to the dosage, depending on the age and condition of the patient, and the precise dosage will be ultimately at the discretion of the attendant physician or veterinarian. The dosage will also depend on the route of administration and the particular compound selected. A suitable dose range is for example 0.1 mg/kg to 30 mg/kg bodyweight per day calculated as the free base, for example 3 mg/kg to 15 mg/kg. A suitable dose for an adult human is for example in the range of 200 mg to 900 mg per day.

The sodium channel antagonists may, if desired, be administered in combination with one or more other therapeutic agents and formulated for administration by any convenient route in a conventional manner. Appropriate doses will be readily appreciated by those skilled in the art.

DESCRIPTION OF THE DETAILED EMBODIMENTS

EXAMPLE 1

Figure 1:
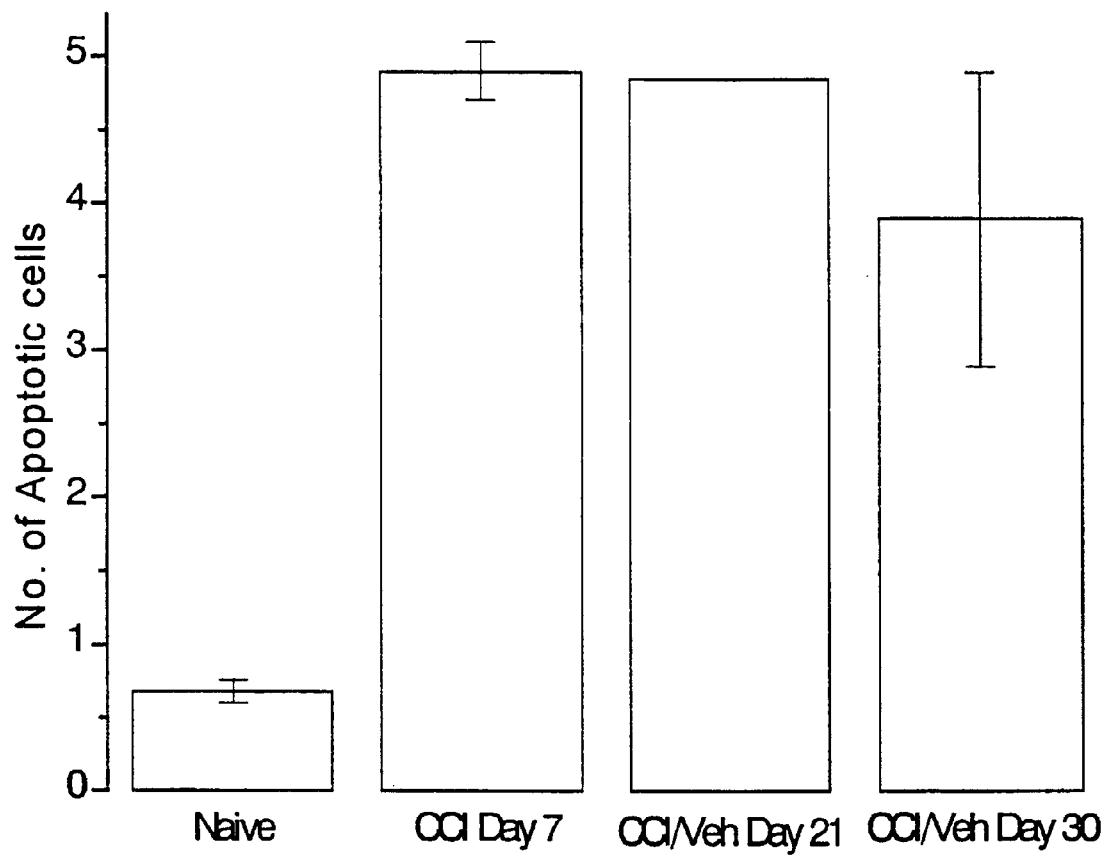
FIG. 1. Numbers of neurones undergoing apoptosis in the naive animal and at three time points after CCI surgery (7,21 and 30 days). Neuronal apoptosis is elevated up to 30 days post surgery.

Sodium channel antagonists have been shown to prevent neuronal apoptosis in the neonatal rat 1 and 3 days after sciatic nerve axotomy. Newborn animals received a single pre-emptive injection of R(–)-2,4-diamino-5-(2,3-dichlorophenyl)-6-fluoromethyl pyrimidine, substantially free of the corresponding S(+)enantiomer (4030W92) (10 mg/kg, s/c). Twenty minutes later the animals were anaesthetised by hypothermia, the nerve exposed and transected at the mid thigh level. The extent of neuronal and glial apoptosis was investigated using the TUNEL technique combined with Hoechst 33342 (Sigma) and immunohistochemistry. The ipsilateral and contralateral L5 dorsal root ganglions were compared and the 4030W92 treated group was compared to vehicle treated controls and to animals that received an injection of 4030W92 alone, ie. no nerve transection. There was a significant reduction in the number of apoptotic neurons observed at 24 hours.

EXAMPLE 2

Adult male random hooded rats were either chronic constriction injury (CCI) or sham operated at day 0. Dosing with vehicle, 4030W92 (10 mg/kg) or 4082W92 (10 mg/kg) was from day 12 to day 25. At time points 7, 14, 21, 27 and 30 days post surgery animals (n=3 per group except for naives) were sacrificed by exsanguination after behavioural testing as described below. Naive animals were all sacrificed 30 days post surgery. L4 and L5 dorsal root ganglias were removed and placed in a freezing medium for sectioning. Sections (14 μm) were cut using a freezing cryostat (Leica) and placed on poly (L) lysine coated slides. These were post-fixed in 4% paraformaldehyde (Sigma) for 20 minutes, dehydrated through alcohol and kept at –80° until required. On the day of staining, the sections were rehydrated through alcohol and placed in phosphate buffered saline (PBS) for at least 15 minutes. They were incubated with the fluorescent nuclear stain Hoechst 33342 (1 μg/ml) (Sigma) for 4 minutes and then washed extensively with PBS. After drying, the slides were mounted with Vectashield mounting medium (Vector Labs) and coverslipped. The slides could be kept in the dark for up to 6 weeks without fading.

Figure 2:
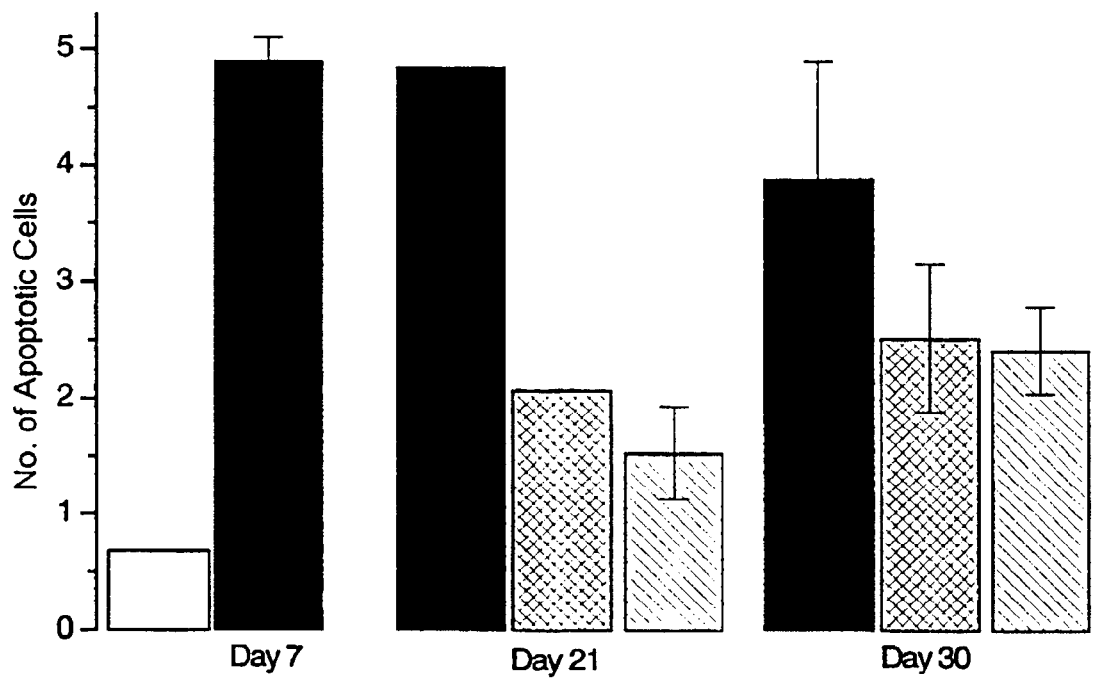
FIG. 2. The number of neurones undergoing apoptosis decreases when CCI animals (n=3 day 7, n=2 day 21, n=3 day 30) are treated with the sodium channel blocker 4030W92 10 mgKg$^{-1}$ (crossed bars) and 4082W92 10 mgkg$^{-1}$ (slanted bars) (numbers per group as for vehicle timepoints). Levels in the vehicle treated animals (solid bars) remained constant over the time course. In CCI animals at all time points there were significantly more apoptotic cells than in naive animals (n=4) (hollow bar).

The sections were studied under the microscope (Leica) at 400× for morphological signs of apoptosis—nuclear condensation, membrane blebbing and presence of apoptotic bodies (Trump 1997 supra). Cells were assigned as neurones or glia depending on their size, location, and general morphology. Four fields from each section were selected at random, the number of apoptotic cells and total number of cells was counted in each and then mean figures for each group were calculated. This analysis was carried out blind. The results are shown in FIGS. 1 and 2. It is clear from these results that CCI provides a suitable model of apoptosis following injury (FIG. 1) and that the sodium ion channel blockers 4030W92 and 4082W92 significantly reduced sensory neuronal apoptosis at day 30 (FIG. 2). Glial apoptosis was unaffected (results not shown).

Behavioural Test

Under isoflurane anaesthesia, the common left sciatic nerve of male Random Hooded rats (180–200 g) was exposed at mid-thigh level. Four ligatures of chromic gut (4.0) were tied loosely around the nerve with a 1 mm spacing between each. The wound was then closed and secured with suture clips. The surgical procedure was identical for the sham operated animals except the sciatic nerve was not ligated. The rats were allowed a period of seven days to recover from the surgery before behavioural testing began.

The effect on Chronic Constriction Injury-induced decrease in mechanical paw withdrawal threshold was measured using an algesymeter (Randall L O, Selitto J J. A method for measurement of analgesic activity on inflamed tissue. Arch. Int. Pharmacodyn. 1957; 61:409–419). In brief, from 7 days post surgery onwards every 2 or 3 days the animals were tested for mechanical hypersensitivity by applying an increasing weight (16 gram per second) to the dorsal surface of each hindpaw until the rat attempted to remove the paw. The increasing weight was halted at this point and the weight recorded and expressed as mechanical paw withdrawal threshold. The maximum weight applied in this model was 250 gram. Drug was administered once the hypersensitivity was maximal which in this case was at day 12.

The presence of mechanical allodynia was assessed using Von Frey Hair monofilaments (range:4.19–84.96 g). The rats were lightly restrained and placed upon a metal grid floor. The monofilaments were applied to the plantar surface of the hindpaws from below the grid. The lowest monofilament to produce a withdrawal was the response recorded.

Administration of the sodium ion channel blockers 4030W92 significantly reversed the reduction in thresholds caused by CCI in these tests.

The application of which this description and claims forms part may be used as a basis for priority in respect of any subsequent application. The claims of such subsequent application may be directed to any feature or combination of features described herein. The claims may take the form of product, composition, process or use claims and may include, by way of example, one or more of the following claims.

What is claimed is:

1. A method for the treatment of a mammal, suffering from or susceptible to diseases mediated by, or exacerbated by, neuronal apoptosis, comprising administration of an effective amount of a sodium channel antagonist.

2. The method of claim 1 wherein the neuronal apoptosis is sensory neuronal apoptosis.

3. The method of claim 1 wherein the sodium channel antagonist is a compound of formula (I)

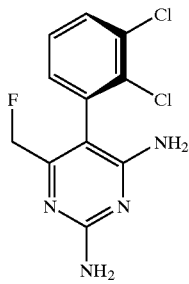

(I)

and acid addition salts thereof or formula (II)

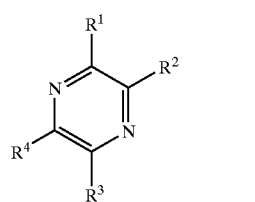

(II)

wherein

R$^1$ is selected from the group consisting of phenyl substituted by one or more halogen atoms, naphthyl and naphthyl substituted by one or more halogen atoms;

R$^2$ is selected from the group consisting of —NH$_2$ and —NHC(=O)R$^a$;

R$^3$ is selected from the group consisting of —NR$^b$R$^c$, —NHC(=O) R$^a$ and hydrogen;

R$^4$ is selected from the group consisting of hydrogen, —C$_{1-4}$ alkyl, —C$_{1-4}$ alkyl substituted by one or more halogen atoms, —CN, —CH$_2$OH, —CH$_2$OR$^d$ and —CH$_2$S(O)$_x$R$^d$;

wherein

R$^a$ represents C$_{1-4}$ alkyl or C$_{3-7}$cycloalkyl, and

R$^b$ and R$^c$, which may be the same or different, are selected from hydrogen and C$_{1-4}$ alkyl, or together with the nitrogen atom to which they are attached, form a 6-membered nitrogen containing heterocycle, which heterocycle can be further substituted with one or more C$_{1-4}$ alkyl;

R$^d$ is selected from C$_{1-4}$ alkyl or C$_{1-4}$ alkyl substituted by one or more halogen atoms;

x is an integer zero, one or two;

and pharmaceutically acceptable derivatives thereof;

with the proviso that R$^1$ does not represent;

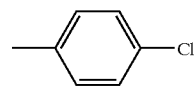

when R$^2$ is —NH$_2$, and both R$^3$ and R$^4$ are hydrogen.

4. The method of claim 1 wherein the sodium channel antagonist is selected from the group consisting of i) 3,5-diamino-6-(2,3-dichlorophenyl)-1,2,4-triazine;

ii) R(−) and S(+)-2,4-diamino-5-(2,3-dichlorophenyl)-6-fluoromethylpyrimidine;

iii) 2,6-diamino-3-(2,3,5-trichlorophenyl)pyrazine;

iv) 5-amino-6-[2,3,5-trichlorophenyl]-1,2,4-triazine and pharmaceutically acceptable derivatives thereof;

v) (+/−)5-(2,3-dichlorophenyl)-6-trifluoromethyl-2,4-diaminopyrimidine and vi) (+/−)5-(2,6-dichlorophenyl)-6-methyl-2,4-diaminopyrimidine and their enantiomeric forms; and vii) 5-carboxamido-2,6-diamino-3-(2,3,5-trichlorophenyl)pyrazine.

5. The method of claim 1 wherein the sodium channel antagonist is R(−)-2,4-diamino-5-(2,3-dichlorophenyl)-6-fluoromethyl pyrimidine, substantially free of the corresponding S(+)enantiomer.

6. The method of claim 1 wherein the mammal is man.

7. The method of claim 1 wherein said mammal is suffering from or susceptible to multiple sclerosis.

8. The method of claim 7 wherein the sodium channel antagonist is a compound of formula (I),

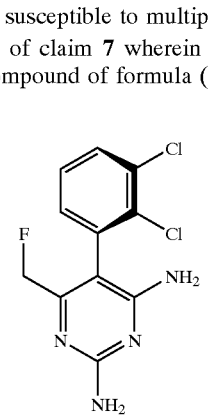

(I)

and acid addition salts thereof or formula (II),

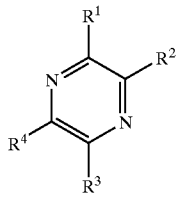
(II)

wherein
R$^1$ is selected from the group consisting of phenyl substituted by one or more halogen atoms, naphthyl and naphthyl substituted by one or more halogen atoms;
R$^2$ is selected from the group consisting of —NH$_2$ and —NHC(=O)R$^a$;
R$^3$ is selected from the group consisting of —NR$^b$R$^c$, —NHC(=O)R$^a$ and hydrogen;
R$^4$ is selected from the group consisting of hydrogen, —C$_{1-4}$ alkyl (preferably methyl), —C$_{1-4}$ alkyl (preferably methyl) substituted by one or more halogen atoms, —CN, —CH$_2$OH, —CH$_2$OR$^d$ and —CH$_2$S(O)$_x$R$^d$;
wherein
R$^a$ represents C$_{1-4}$ alkyl or C$_{3-7}$cycloalkyl, and
R$^b$ and R$^c$, which may be the same or different, are selected from hydrogen and C$_{1-4}$ alkyl, or together with the nitrogen atom to which they are attached, form a 6-membered nitrogen containing heterocycle, which heterocycle can be further substituted with one or more C$_{1-4}$ alkyl;
R$^d$ is selected from C$_{1-4}$ alkyl or C$_{1-4}$ alkyl substituted by one or more halogen atoms;
x is an integer zero, one or two;
nd pharmaceutically acceptable derivatives thereof;
with the proviso that R$^1$ does not represent;

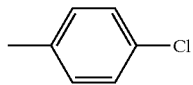

when R$^2$ is —NH$_2$, and both R$^3$ and R$^4$ are hydrogen. Particularly preferred is 2,6-diamino-3-(2,3,5-trichlorophenyl)pyrazine and pharmaceutically acceptable derivatives thereof.

9. The method of claim 7 wherein the sodium channel antagonist is selected from the group consisting of
i) 3,5-diamino-6-(2,3-dichlorophenyl)-1,2,4-triazine;
ii) R(–) and S(+)-2,4-diamino-5-(2,3-dichlorophenyl)-6-fluoromethylpyrimidine;
iii) 2,6-diamino-3-(2,3,5-trichlorophenyl)pyrazine;
iv) 5-amino-6-[2,3,5-trichlorophenyl]-1,2,4-triazine and pharmaceutically acceptable derivatives thereof;
v) (+/–)5-(2,3-dichlorophenyl)-6-trifluoromethyl-2,4-diaminopyrimidine and
vi) (+/–)5-(2,6-dichlorophenyl)-6-methyl-2,4-diaminopyrimidine and their enantiomeric forms; and
vii) 5-carboxamido-2,6-diamino-3-(2,3,5-trichlorophenyl)pyrazine.

10. The method of claim 7 wherein the sodium channel antagonist is R(–)-2,4-diamino-5-(2,3-dichlorophenyl)-6-fluoromethyl pyrimidine, substantially free of the corresponding S(+)enantiomer.

11. A method for delaying or halting the progression of diseases selected from pain states following nerve insult, neurodegenerative diseases and inflammation in a mammal, comprising administration of an effective amount of a sodium channel antagonist.

12. The method of claim 11 wherein the sodium channel antagonist is a compound of formula (I),

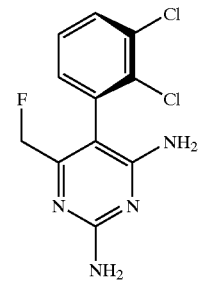
(I)

and acid addition salts thereof or formula (II)

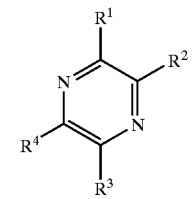
(II)

wherein
R$^1$ is selected from the group consisting of phenyl substituted by one or more halogen atoms, naphthyl and naphthyl substituted by one or more halogen atoms;
R$^2$ is selected from the group consisting of —NH$_2$ and —NHC(=O)R$^a$;
R$^3$ is selected from the group consisting of —NR$^b$R$^c$, —NHC(=O)R$^a$ and hydrogen;
R$^4$ is selected from the group consisting of hydrogen, —C$_{1-4}$ alkyl, —C$_{1-4}$ alkyl substituted by one or more halogen atoms, —CN, —CH$_2$OH, —CH$_2$OR$^d$ and —CH$_2$S(O)$_x$R$^d$;
wherein
R$^a$ represents C$_{1-4}$ alkyl or C$_{3-7}$cycloalkyl, and
R$^b$ and R$^c$, which may be the same or different, are selected from hydrogen and C$_{1-4}$ alkyl, or together with the nitrogen atom to which they are attached, form a 6-membered nitrogen containing heterocycle, which heterocycle can be further substituted with one or more C$_{1-4}$ alkyl;
R$^d$ is selected from C$_{1-4}$ alkyl or C$_{1-4}$ alkyl substituted by one or more halogen atoms;
x is an integer zero, one or two;
and pharmaceutically acceptable derivatives thereof;
with the proviso that R$^1$ does not represent;

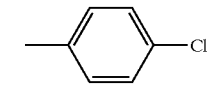

when R$^2$ is —NH$_2$, and both R$^3$ and R$^4$ are hydrogen.

13. The method of claim 11 wherein the sodium channel antagonist is selected from the group consisting of i) 3,5-diamino-6-(2,3-dichlorophenyl)-1,2,4-triazine;
ii) R(−) and S(+)-2,4-diamino-5-(2,3-dichlorophenyl)-6-fluoromethylpyrimidine;
iii) 2,6-diamino-3-(2,3,5-trichlorophenyl)pyrazine;
iv) 5-amino-6-[2,3,5-trichlorophenyl]-1,2,4-triazine and pharmaceutically acceptable derivatives thereof;
v) (+/−)5-(2,3-dichlorophenyl)-6-trifluoromethyl-2,4-diaminopyrimidine and
vi) (+/−)5-(2,6-dichlorophenyl)-6-methyl-2,4-diaminopyrimidine and their enantiomeric forms; and
vii) 5-carboxamido-2,6-diamino-3-(2,3,5-trichlorophenyl)pyrazine.

14. The method of claim 11 wherein the sodium channel antagonist is R(−)-2,4-diamino-5-(2,3-dichlorophenyl)-6-fluoromethyl pyrimidine, substantially free of the corresponding S(+)enantiomer.

15. The method of claim 11 wherein the mammal is man.

* * * * *